United States Patent
Thoma et al.

(10) Patent No.: US 9,332,948 B2
(45) Date of Patent: May 10, 2016

(54) SYSTEM AND METHOD FOR PATIENT POSITIONING IN CONE-BEAM TOMOGRAPHY

(75) Inventors: Dieter Thoma, Einhausen (DE); Christian Beckhaus, Darmstadt (DE)

(73) Assignee: SIRONA DENTAL SYSTEMS, GmbH, Bensheim (DE)

(*) Notice: Subject to any disclaimer, the term of this patent is extended or adjusted under 35 U.S.C. 154(b) by 61 days.

(21) Appl. No.: 12/992,048

(22) PCT Filed: May 15, 2009

(86) PCT No.: PCT/EP2009/055896
§ 371 (c)(1),
(2), (4) Date: Mar. 9, 2011

(87) PCT Pub. No.: WO2009/138483
PCT Pub. Date: Nov. 19, 2009

(65) Prior Publication Data
US 2011/0152675 A1    Jun. 23, 2011

Related U.S. Application Data

(63) Continuation of application No. 12/122,269, filed on May 16, 2008, now abandoned.

(51) Int. Cl.
*A61B 5/05* (2006.01)
*A61B 6/14* (2006.01)
(Continued)

(52) U.S. Cl.
CPC . *A61B 6/14* (2013.01); *A61B 6/032* (2013.01); *A61B 6/04* (2013.01); *A61B 6/0421* (2013.01)

(58) Field of Classification Search
CPC .......... A61B 6/14; A61B 6/032; A61B 19/20; A61B 19/203; A61B 19/5244; A61B 19/52; A61B 19/5212; A61B 6/04; A61B 6/0421
USPC .............. 600/407–429; 378/4–38; 433/54–68
See application file for complete search history.

(56) References Cited

U.S. PATENT DOCUMENTS

| | | | |
|---|---|---|---|
| 3,099,441 A | | 7/1963 | Ries |
| 4,782,503 A | * | 11/1988 | Molitor ............ A61B 6/14 378/169 |

(Continued)

FOREIGN PATENT DOCUMENTS

| | | | |
|---|---|---|---|
| JP | H09-509342 A | 9/1997 | |
| JP | H10-314165 A | 12/1998 | |

(Continued)

OTHER PUBLICATIONS

Japanese Patent Office, Office Action issued in connection with Japanese Application No. 2011-508932, May 14, 2013, 4 pages, with translation.

*Primary Examiner* — Sanjay Cattungal
(74) *Attorney, Agent, or Firm* — Fitzpatrick, Cella, Harper & Scinto

(57) ABSTRACT

A device for positioning a patient within an image volume of a cone-beam tomography system. The device includes a volume indicator adapted to indicate at least a front boundary of the image volume and having a horizontal indicator for horizontal alignment. The device also includes a head clamp adapted to position at least a portion of the head of the patient within the front boundary of the image volume indicated by the volume indicator.

22 Claims, 8 Drawing Sheets

(51) Int. Cl.
*A61B 6/03* (2006.01)
*A61B 6/04* (2006.01)

(56) References Cited

U.S. PATENT DOCUMENTS

| | | | |
|---|---|---|---|
| 4,971,060 A | 11/1990 | Schneider et al. ......... 128/653.1 |
| 5,197,965 A | 3/1993 | Cherry et al. |
| 5,254,079 A | 10/1993 | Agbodoe et al. |
| 5,269,034 A | 12/1993 | Day et al. |
| 5,318,509 A | 6/1994 | Agbodoe |
| 5,375,156 A | 12/1994 | Kuo-Petravic et al. |
| 5,400,255 A | 3/1995 | Hu |
| 5,461,650 A | 10/1995 | Tam |
| 5,537,704 A | 7/1996 | Dinkler |
| 5,565,684 A | 10/1996 | Gullberg et al. |
| 5,662,111 A * | 9/1997 | Cosman ................ A61B 19/20 600/417 |
| 5,692,027 A * | 11/1997 | Yoshimura .............. A61B 6/14 378/116 |
| 5,802,134 A | 9/1998 | Larson et al. |
| 5,881,122 A | 3/1999 | Crawford et al. |
| 5,887,047 A | 3/1999 | Bailey et al. |
| 5,909,477 A | 6/1999 | Crawford et al. |
| 5,921,927 A | 7/1999 | McArdle ....................... 600/425 |
| 5,954,647 A | 9/1999 | Bova et al. |
| 5,971,997 A | 10/1999 | Guthrie et al. |
| 5,980,535 A | 11/1999 | Barnett et al. |
| 5,984,930 A | 11/1999 | Maciunas et al. |
| 6,130,929 A | 10/2000 | Saha |
| 6,169,780 B1 * | 1/2001 | Yoshimura .............. A61B 6/14 378/38 |
| 6,201,849 B1 | 3/2001 | Lai |
| 6,243,439 B1 * | 6/2001 | Arai ...................... A61B 6/032 378/162 |
| 6,256,365 B1 | 7/2001 | Lai |
| 6,256,366 B1 | 7/2001 | Lai |
| 6,259,943 B1 * | 7/2001 | Cosman ................ A61B 19/20 600/417 |
| 6,289,074 B1 * | 9/2001 | Arai ........................ A61B 6/14 378/38 |
| 6,480,565 B1 | 11/2002 | Ning |
| 6,654,440 B1 | 11/2003 | Hsieh |
| 6,817,762 B2 | 11/2004 | Proksa |
| 6,842,502 B2 | 1/2005 | Jaffray et al. |
| 6,865,254 B2 | 3/2005 | Nafstadius |
| 6,987,831 B2 | 1/2006 | Ning |
| 7,103,141 B2 | 9/2006 | Sonobe et al. |
| 7,154,986 B2 | 12/2006 | Hein et al. |
| 7,486,759 B2 * | 2/2009 | Suzuki ..................... A61B 6/14 378/38 |
| 7,787,586 B2 * | 8/2010 | Yoshimura ............. A61B 6/032 378/38 |
| 2005/0277086 A1 * | 12/2005 | Arai ..................... A61C 19/045 433/54 |
| 2006/0200246 A1 * | 9/2006 | Lambrecht .............. A61F 2/442 623/17.16 |
| 2007/0190481 A1 * | 8/2007 | Schmitt .............. A61C 13/0004 433/68 |
| 2007/0280408 A1 | 12/2007 | Zhang |
| 2008/0137802 A1 * | 6/2008 | Suzuki ..................... A61B 6/14 378/4 |
| 2009/0052617 A1 * | 2/2009 | Sadakane ............... A61B 6/032 378/38 |

FOREIGN PATENT DOCUMENTS

| | | |
|---|---|---|
| JP | 2002-301089 A | 10/2002 |
| JP | 2003-245277 A | 9/2003 |
| WO | 95/21571 A1 | 8/1995 |

* cited by examiner

SYSTEM AND METHOD FOR PATIENT POSITIONING IN CONE-BEAM TOMOGRAPHY

CROSS REFERENCE TO RELATED APPLICATIONS

This application is a National Stage filing under 35 U.S.C. §371 of International Application No. PCT/EP2009/055896, filed May 15, 2009, and claims priority to U.S. patent application Ser. No. 12/122,269, filed May 16, 2008.

BACKGROUND OF THE INVENTION

1. Field of the Invention

The present invention generally relates to the field of cone-beam tomography systems, and more particularly to systems and methods for positioning patients in such systems.

2. Related Art

Cone beam computed tomography (CT) systems are widely employed and have many applications. In particular, they are becoming increasingly useful and prevalent within the dental industry. Such systems can be useful in the dental industry for a number of diagnostic and treatment procedures, including implants, temporomandibular joint (TMJ), orthodontics, impaction, orthognathic surgery, airway/sleep apnea studies, etc.

In x-ray imaging, an x-ray image of an object is created when x-rays are transmitted from a source through the object and collected on an image sensor or detector. The amount of x-ray radiation that reaches the sensor is related to the amount of attenuation that the x-ray encounters in the corresponding path through the object.

Broadly, computed tomography is a technique of reconstructing a three-dimensional image from a sequence of two-dimensional projection images. CT systems capture two-dimensional images and employ reconstruction algorithms to create three-dimensional images. Multiple projection images are used at different source-detector radiation angles relative to the object to obtain the required information to isolate a single plane in the object or create a complete three-dimensional reconstruction.

Cone-beam tomography directly captures three-dimensional information in a single scan. In cone-beam tomography, an x-ray source generates a cone-shaped illumination that is captured by a two-dimensional area detector. The source-detector assembly is scanned around the patient, resulting in the capture of a sequence of two-dimensional projection images. A direct three-dimensional reconstruction is then performed.

In a cone-beam tomography examination, it is useful for the patient to remain stationary in an assumed volume of space while the x-ray source and the source-detector assembly are scanned around the patient to capture the sequence of two-dimensional images in that assumed volume of space. However, it has been discovered that positioning the patient properly within that image volume, such as an orthodontic patient, presents a great clinical challenge and can affect image quality.

SUMMARY OF THE INVENTION

The present invention can provide in at least one embodiment, a system, method, apparatus, and program that can achieve accurate and precise positioning of a patient in a cone-beam tomography examination, such as for an orthodontic patient.

Before describing the present invention in detail, it is to be understood that the practice of the present invention employs, unless otherwise indicated, conventional methods of cone-beam tomography and processing as known by those having ordinary skill in the art. The present invention is not limited to particular formulations or process parameters as such may, of course, vary.

The present invention in accordance with one embodiment provides a device for positioning a patient within an image volume of a cone-beam tomography system. The device includes a head clamp having an ear tube attached at each of two ends adapted to fix the patient in the auditory canals, and having a head support adapted to further restrict movement of the patient. The head clamp registers the condyles of the patient with respect to the image volume.

The head support may restrict movement of the patient in the front or rear directions. The head clamp may further include a volume indicator adapted to indicate at least a front boundary of the image volume and having a horizontal indicator for horizontal alignment.

The present invention in accordance with another embodiment provides a device for positioning a patient within an image volume of a cone-beam tomography system. The device includes a volume indicator adapted to indicate at least a front boundary of the image volume and having a horizontal indicator for horizontal alignment. The device also includes a head clamp adapted to position at least a portion of the head of the patient within the front boundary of the image volume indicated by the volume indicator.

The head clamp may include (1) a plurality of ear tubes at each end adapted to restrict lateral movement of a head of the patient and facilitate alignment of the head of the patient in a substantially horizontal plane relative to the horizontal structure, and (2) a forehead alignment mechanism adapted to restrict forward movement of the head of the patient. The head clamp may be adjustable. Further, the front boundary of the image volume may be spherical or cylindrical, and the horizontal indicator may be a laser.

The device may further include a measuring unit adapted to measure a position of the head clamp, a calculating unit adapted to calculate a position of the patient based on a result obtained by the measuring unit, and a directing unit adapted to direct re-positioning of the patient based on a result obtained by the calculating unit.

The device may further include a measuring unit adapted to measure a position of the head clamp, a calculating unit adapted to calculate a position of the patient based on a result obtained by the measuring unit, and a programming unit adapted to program a scanning trajectory of the cone-beam tomography system based on a result obtained by the calculating unit.

The present invention in accordance with one embodiment provides a method of positioning a patient within an image volume for a cone-beam tomography examination using a visual aid, including (a) restricting lateral movement of a head of the patient, (b) aligning the head of the patient in a substantially horizontal plane relative to a horizontal indicator of the visual aid, (c) restricting forward movement of the head of the patient, and (d) checking that at least a portion of the head of the patient is within a front boundary of the image volume defined by the visual aid. The front boundary of the image volume may be spherical or cylindrical.

The present invention in accordance with one embodiment provides a method of performing a cone-beam tomography examination of a patient, including (a) restricting lateral movement of a head of the patient, (b) aligning the head of the patient in a substantially horizontal plane relative to a horizontal indicator of a volume indicator, (c) restricting forward movement of the head of the patient, (d) checking that at least a portion of the head of the patient is within a front boundary of an image volume defined by the volume indicator, (e) rotating an x-ray source and a detector around the head of the patient to create a plurality of two-dimensional images, and (f) creating a three-dimensional image based on the plurality of two-dimensional images.

Further features and advantages of the present invention as well as the structure and operation of various embodiments of the present invention are described in detail below with reference to the accompanying drawings.

BRIEF DESCRIPTION OF THE DRAWINGS

The features and advantages of the present invention will become more apparent from the detailed description set forth below when taken in conjunction with the drawings in which like reference numbers indicate identical or functionally similar elements.

DETAILED DESCRIPTION

Figure 1:
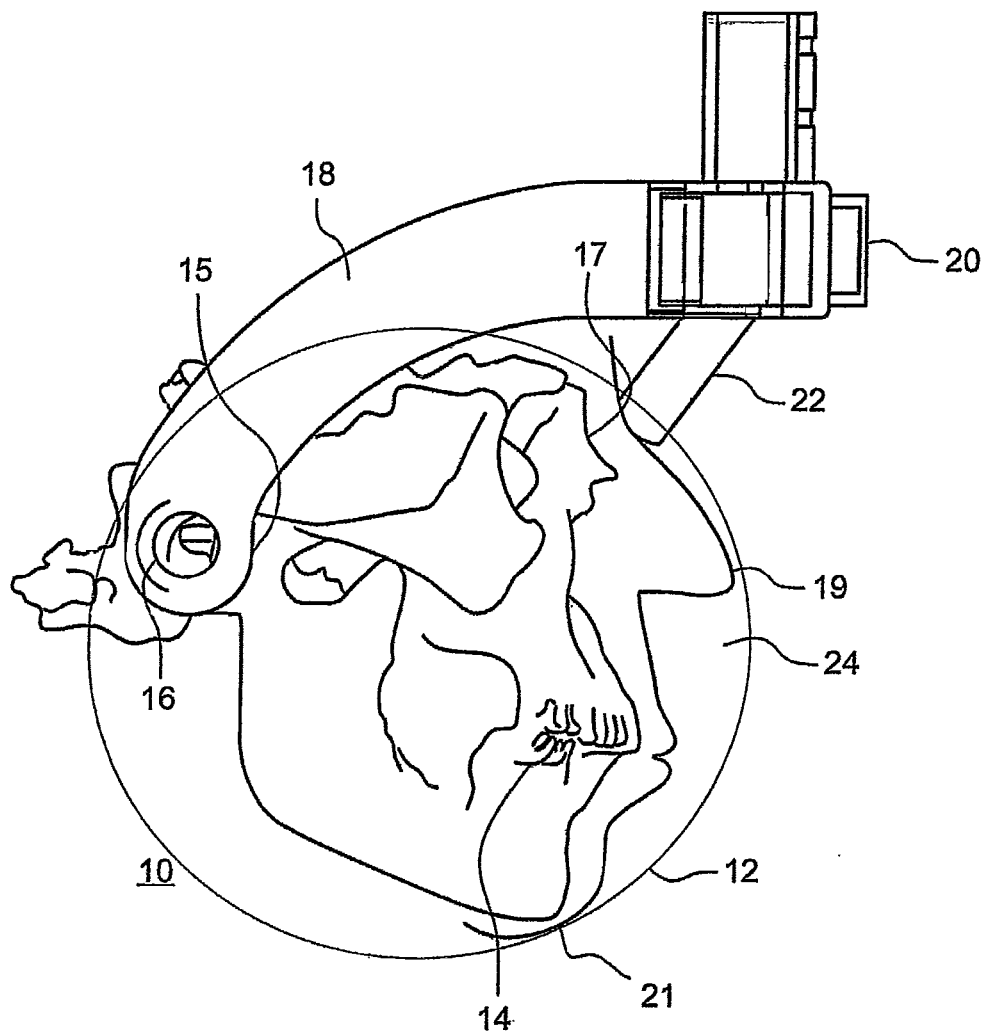
FIG. 1 is an illustration showing a portion of a device for orthodontic patient positioning in cone-beam tomography according to an embodiment of the present invention.

Typical positioning aids for patients in CT or cone-beam tomography, as known in the art, are generally placed below a patient's chin, on the back of the head, on the lateral aspects of the head (sometimes within the ears), and between the patient's teeth. For example, the patient typically sits in a chair, rests his chin on a chin rest, fits ear tubes into his ears, and bites down on a bite block, thereby restricting the patient's movement and aligning him for the cone-beam examination.

In known techniques, based upon such positioning tools, the clinician attempts to position the patient so that the relevant anatomical landmarks, e.g., the condyles or the soft tissue silhouette, will appear in the image volume of the scan. However, it has been discovered that patient positioning using such techniques can be difficult, inefficient, and, if the end result is not accurate, can require multiple exposures and unintended dosage. Typically, the most clinically accurate cone-beam tomography images require that a patient is positioned with the condyles or the soft tissue silhouette coincident with the machine's image volume. Using known techniques it can be difficult to register the condyles or soft tissue silhouette within the image volume, particularly since the features of each patient can vary, and to keep the patient tightly positioned within that volume.

Furthermore, it has been discovered that using a chin rest as in known techniques, it can be difficult to fix a patient with his or her mouth closed and obtain suitable images, since the chin rest can compress the soft tissue of the patient's chin.

Moreover, it has been discovered that using a bite block as in known techniques, such as for an orthodontic patient, can distort the relationship (e.g., in distances and angles) between various anatomic landmarks that an orthodontist is interested in. Accordingly, such distortion can prevent or reduce the ability to obtain accurate occlusal measurements.

The present invention offers a fresh approach, and provides, at least in one embodiment, a system, method, apparatus, and program for orthodontic patient positioning in cone-beam tomography. In particular, the present invention provides, at least in one embodiment, a system, method, apparatus, and program for registering the condyles or the soft tissue silhouette of the patient within the imaging volume of a cone-beam tomography machine. Whereas a variety of positioning aids are known and employed within commercial systems, it has been discovered that such positioning aids are apt to be inaccurate or cumbersome, or both, and can often result in an image of only modest quality.

Accordingly, accurate registering of the patient's condyles or soft tissue silhouette with regard to the image volume can be achieved using the present invention, so that enhanced cone-beam tomography images can be produced. Because cone-beam tomography scans typically have limited x-ray size, the present invention is advantageous in that it can optimize the scan by increasing the amount of anatomy that is registered within the image volume of the scan. Accordingly, the present invention in accordance with an example embodiment can provide a cone-beam tomography system for a patient using simple positioning and accurate imaging.

FIG. 1 is an illustration showing a portion of a device 10 for patient positioning in cone-beam tomography according to an embodiment of the present invention. It is noted that FIG. 1 does not show certain features of the device 10 that are shown in the views of FIGS. 2-5, such as volume indicator 28 that is described below in connection with those figures.

FIG. 1 shows an image volume 12 in which a cone-beam tomography scan captures images of a patient's anatomical features 14, including the condyles 15, wherein the image volume 12 is closed and refernce numeral 12 further represent an outer boundary enclosing that closed image volume. Other features shown in FIG. 1 include the patient's nasion 17, nose tip 19, and a point on the patient's chin 21. It is of course to be understood that the image layer 12 of a cone-beam tomography scan may vary and that various cone-beam tomography scans may have image volumes of varying shapes and sizes.

In FIG. 1, ear tubes 16 located at an end of a position bracket 18 are inserted into the patient's ears for lateral (side to side) positioning, and to aid in horizontal positioning as described further below. A front alignment mechanism 22 aids in positioning, and reference numeral 24 denotes empty space in a front region of the image volume 12 that naturally exists, due to the shape of the patient's face, even with an optimum fit of the patient's anatomical features 14 within the image volume 12. The present invention can enable all of the relevant anatomy to be registered in the image volume 12 of a scan.

Figure 2:
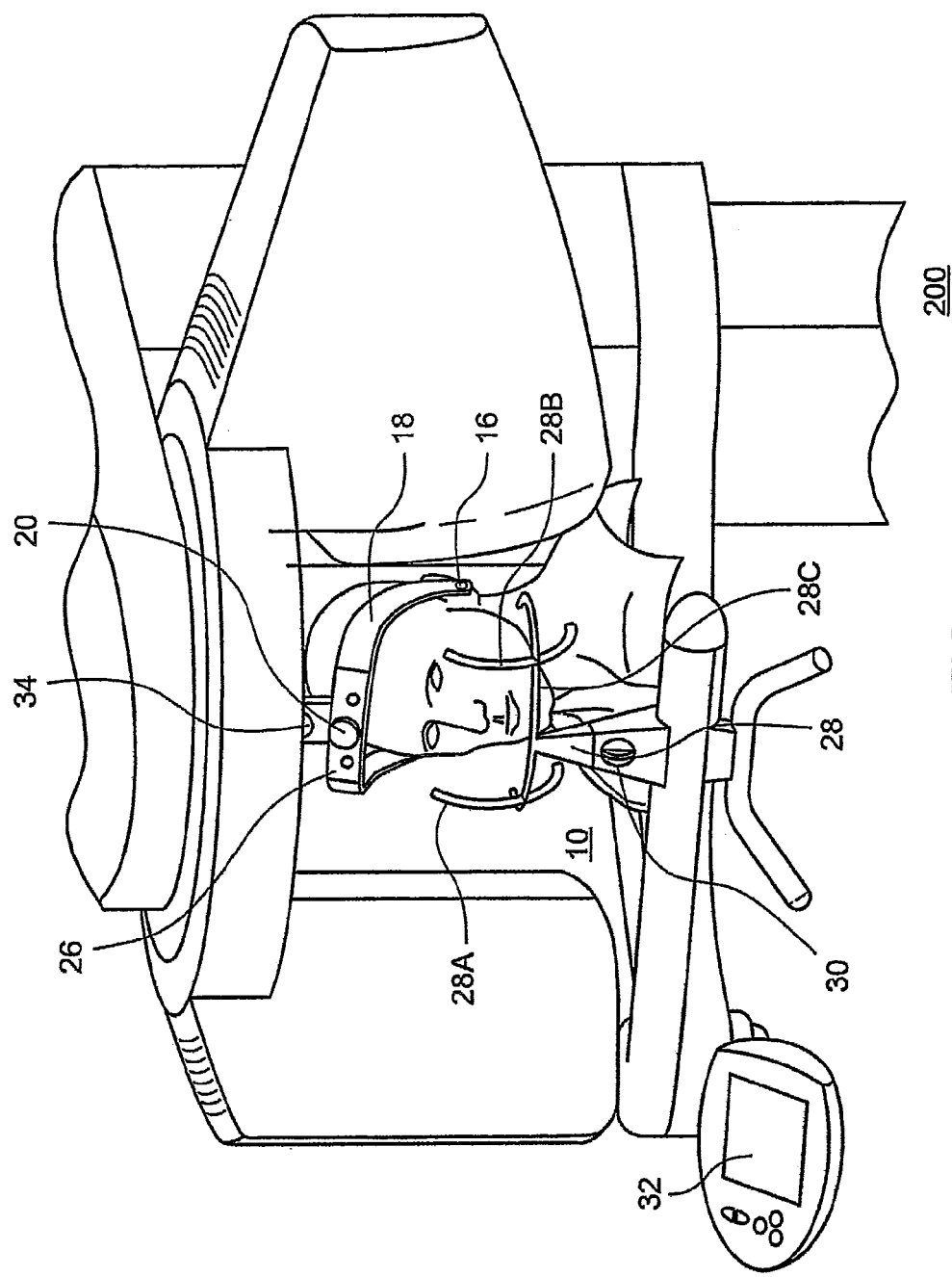
FIG. 2 is a perspective view showing a cone-beam tomography system for orthodontic patient positioning according to an embodiment of the present invention incorporating the device shown in FIG. 1.

FIG. 2 is a perspective view showing a cone-beam tomography system 200 for patient positioning according to an embodiment of the present invention, incorporating the device 10 shown in FIG. 1. More particularly, FIG. 2 is a perspective view including the portion of the device 10 shown in FIG. 1; FIG. 2 also shows certain features of the present invention that are not shown in FIG. 1, including, for example, the volume indicator 28 described below.

The device 10 shown in FIG. 2 includes ear tubes 16, head clamp 18, head rest 26, volume indicator 28, and knobs 20, 30, and 34 (partially obscured in FIG. 2). The head rest 26 aids in front positioning of a patient's head and in stabilization of a suitable angular position of the patient's occlusal layer. The position bracket or head clamp 18, together with the ear tubes 16 located at the ends of the head clamp 18, aid in lateral and horizontal positioning of the patient. In particular, the ear tubes 16, which are gently fitted into the patient's ears by the clinician, can operate to restrict lateral (side to side) movement and can enable the clinician to pivotally adjust or tilt the patient's head about an imaginary axis through the ear tubes for horizontal alignment as further described below. Accordingly, due to the relatively short distance between the condyles and the auditory canal, the ear tubes can enable the patient's condyles or soft tissue silhouette to be registered within the image volume of the cone-beam tomography system 200, such that the physical space to be occupied by the relevant anatomical features of the patient can be related to the image volume.

The knobs 20 and 34 enable the clinician to adjust the position of the head rest 26 and the head clamp 18 for an individualized or custom patient fit. With knob 20, the width of the head clamp 18 can be adjusted. With knob 34, the vertical movement of the head rest 26 can be released and blocked to adjust the vertical position of the patient. The head rest 26 is adjustable vertically via knob 34 and horizontally via knob 35 (see FIG. 5) to accommodate different patients. The clinician can control the standard functions of the cone-beam tomography system using control panel 32.

The device 10 includes, as noted, a volume indicator 28, which provides a visual aid to further aid in the positioning of a patient so that the patient's condyles or soft tissue silhouette can be registered within the image volume of the cone-beam tomography system 200. The volume indicator 28 in the example embodiment shown in FIG. 2 is comprised of two half-moon or parabolically shaped vertical structures 28a and 28b, along with horizontal structure 28c, which together help define at least a portion of a front boundary that the patient should be positioned within in order for the patient's condyles or soft tissue silhouette to appear within the machine's image volume. That is, the volume indicator 28 indicates the physical space defining at least a portion of the machine's image volume, and aids the clinician in visualizing where the image volume is.

Figure 3:
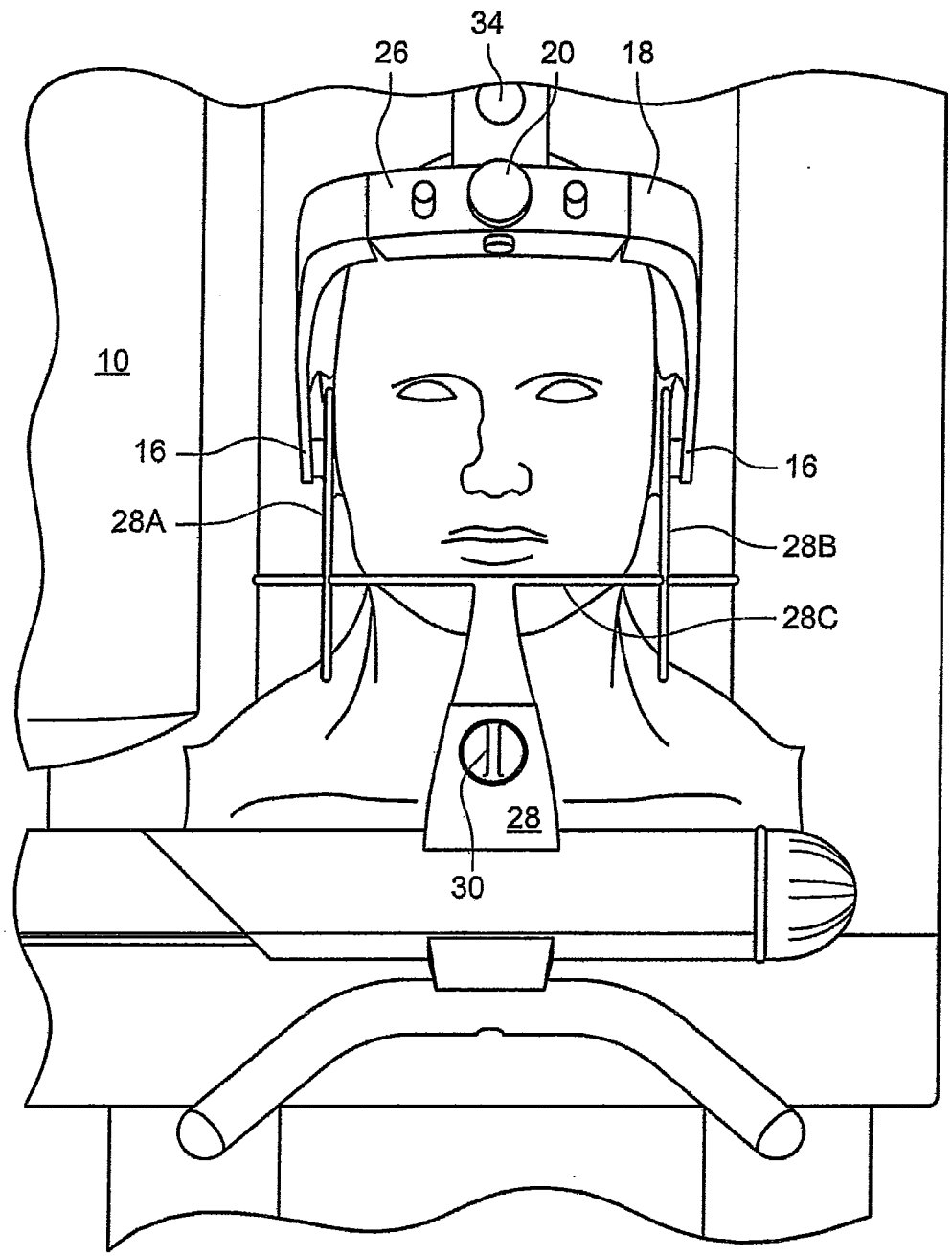
FIG. 3 shows a close-up front view of the device shown in FIG. 2 according to an embodiment of the present invention.
Figure 4:
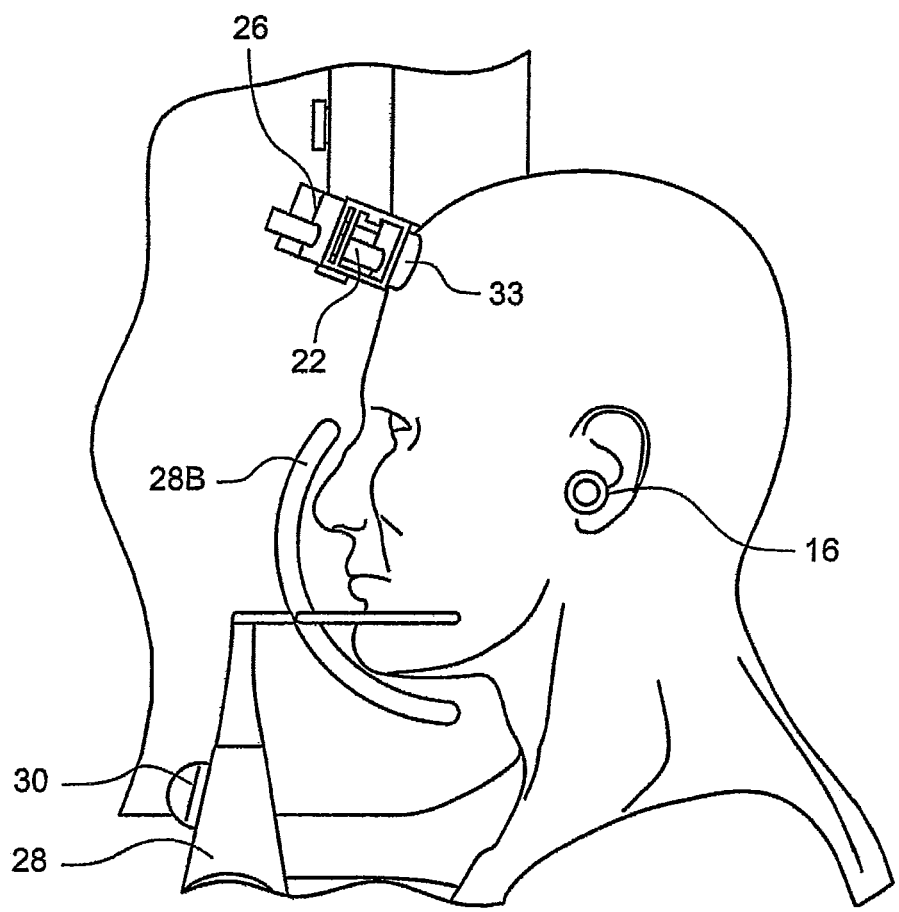
FIG. 4 shows a close-up left side view of a portion of the device shown in FIG. 2 according to an embodiment of the present invention.

FIGS. 3 and 4 show close-up front and left side views, respectively, of the device 10 shown in FIG. 2; though it is to be noted that in FIG. 3 the head clamp 18 is not shown. FIG. 4 includes a forehead pad 33, located at the end of the front alignment mechanism 22, which is part of the head rest 26, and shows a side view of the volume indicator 28 and the physical space defined thereby. A clinician can position a patient using the volume indicator 28 as a visual aid or reference, in order to bring the patient within the outer rim of the image layer as referenced for visual aid purposes by the volume indicator 28. The clinician can optimize imaging by adjusting the forehead pad 33 until it touches the patient's forehead, such that the patient's nose can be fixed at least close to the image volume indicated by the volume indicator 28. Accordingly, the condyles or soft tissue silhouette can be registered in the image layer while, for example, the nose, which does not need to be registered for an orthodontic patient, may not be.

Figure 5:
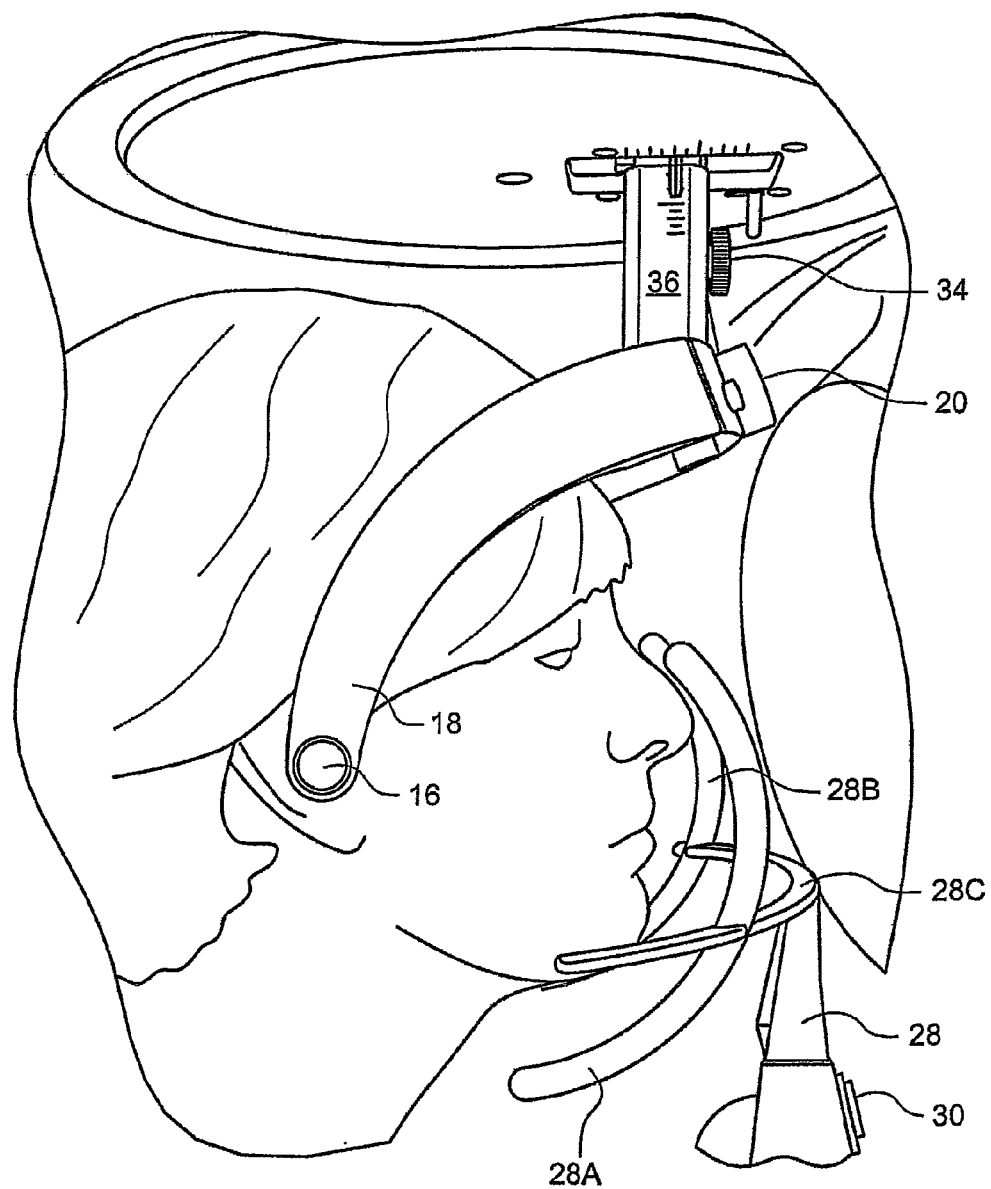
FIG. 5 shows a right side view of the device shown in FIG. 4 according to an embodiment of the present invention.

FIG. 5 is a right side view of the device 10 shown in FIG. 4 according to an embodiment of the present invention. FIG. 5 shows more clearly where the ear tubes 16 are fitted in the patient's ears, and also shows more clearly the adjustability of the head clamp 18. The lines indicating measurement values on vertical support 36 show that the head clamp 18 can be adjusted in the vertical and horizontal directions using knobs 34 and 35.

Accordingly, the device 10 according to an embodiment of the present invention as shown in FIGS. 1-5 is adjustable by the clinician in various ways as described herein in order to aid the clinician in bringing the patient's condyles or soft tissue silhouette within the image volume of the cone-beam tomography system 200 using the volume indicator 28 as a visual aid.

It is of course to be understood that the details of the present invention are not limited by the example embodiment shown in FIGS. 1-5, and that various modifications can be made to this example embodiment, as would readily be understood by a person having ordinary skill in the art. For example, the present invention according to one embodiment can have a rear head pad along with or instead of the forehead pad 33, to provide rear head support. Accordingly, restriction of the patient's head in the forward and backward directions can be achieved, which can prevent the patient from nodding and thereby de-stabilizing his or her head.

Figure 6:
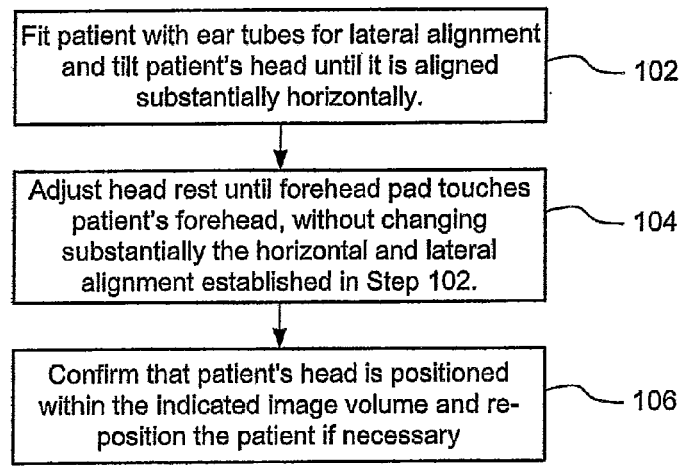
FIG. 6 is a flowchart showing a method for patient positioning in cone-beam tomography according to an embodiment of the present invention.

FIG. 6 is a flowchart showing a method 100 for patient positioning in cone-beam tomography according to an embodiment of the present invention. The method 100 can use a cone-beam tomography system such as system 200 of FIGS. 1-5 which includes positioning device 10. By virtue of the method shown in FIG. 6, the patient's condyles or soft tissue silhouette can be brought within the image volume 12 of the scan performed by the cone-beam tomography system 200, which can result in a more useful image.

In step 102, the clinician brings the patient's head inside the position bracket or head clamp 18. The clinician fits the ear tubes 16 into the patient's ears and pivotally adjusts or tilts the patient's head on an imaginary axis through the ear tubes 16 until the patient's head is in substantial alignment with the horizontal plane defined by the horizontal structure 28c. Accordingly, the patient's head is adjusted or pivoted vertically (i.e., up and down about that imaginary axis) until it is fixed in substantial horizontal alignment with the horizontal structure 28c of the volume indicator 28. This is the preferred position for taking an image. The ear tubes 16 also keep the patient aligned in a substantially vertical or lateral (side to side) direction. Accordingly, the patient's head is aligned substantially horizontally and laterally.

In step 104, the clinician adjusts the forehead pad 33 of the head rest 26 until it touches the patient's forehead, without substantially changing the established horizontal alignment. Thus, the patient is fixed in the head rest 26. In step 106, the clinician confirms that at least a portion of the patient's head is positioned within a front boundary of the image volume as indicated by the volume indicator 28, and the clinician re-positions the patient according to that indicated image volume if necessary. The device 10 may also, in one embodiment, include laser lights or LEDs (not shown) to aid in optimum positioning.

It is noted that by virtue of the method of FIG. 6, the clinician or doctor can determine before the scan whether all relevant anatomic structures can be imaged in one cone-beam tomography scan. If the clinician or doctor determines that all relevant anatomic structures may not be imaged in one scan, however, the clinician can position the patient in favor of, for example, either the soft tissue silhouette (e.g., the nose or chin) or the condyles, depending on which anatomy is more relevant to the specific diagnostic or planning purpose.

As can be seen from the device 10 of FIGS. 1-5 and the method 100 of FIG. 6, the present invention according to one embodiment can utilize at least three points for positioning an orthodontic patient in a cone-beam tomography examination: both of the patient's ears and the patient's forehead. In this embodiment, there are two degrees of freedom available for adjusting the patient: vertically and horizontally, as described. Accordingly, the present invention according to one embodiment can provide a system and method for rigidly fixing the patient in an image volume for a cone-beam scan.

Moreover, the present invention according to one embodiment can enable a representation of the occlusion bite without compressing the soft tissue of the chin region, since the present invention according to one embodiment does not use a chin rest. Using the ear tubes 16 as described herein is advantageous because there is not much soft tissue in between.

Furthermore, the present invention according to one embodiment does not use a bite block for patient positioning. As explained above, a bite block, as in known techniques, such as for an orthodontic patient, can distort the relationship between various anatomic landmarks that an orthodontist is interested in. Accordingly, the present invention according to one embodiment does not use a bite block and can provide more accurate occlusal measurements.

It is of course to be understood that the present invention is not limited to the example embodiments shown in FIGS. 1-6. For example, other embodiments of the volume indicator 28 can be readily envisioned, e.g., depending on the type of detector used. As one example, while the shape of each vertical structure 28a and 28b of the volume indicator 28 is spherical, if a rectangular flatpanel detector is used, the image volume would be cylindric instead of spherical, and the front boundary of the image volume would then be rectangular instead of spherical. Accordingly, the shape of each vertical structure 28a and 28b would be straight, and not spherical, to represent that rectangular front boundary. The present invention is also not limited to only two vertical structures 28a and 28b, and any suitable number of such structures can suffice. Furthermore, instead of the structures 28a, 28b, and 28c being physical or non-electrical elements, any or all of them may be electrical elements such as a laser. Other variations are readily envisioned in view of this description.

In another embodiment of the present invention, the device 10 of FIGS. 1-5 can be used without the volume control 28. That is, the device 10, including, e.g., the ear tubes 16, head clamp 18, front alignment mechanism 22, head rest 26, forehead pad 33, knobs 20, 34, and 35 can be used without the volume control 28. For example, the head clamp 18 including the ear tubes 16 can be used to fix the patient in his auditory canals, and the forehead pad 33 can restrict movement of the patient in the front direction. Or, a rear head pad (not shown) can restrict movement of the patient in the rear direction. Accordingly, the head clamp 18 including the ear tubes 16 can register the relevant anatomy (e.g., the condyles or the soft tissue silhouette) of the patient within the image volume 12. This can provide for rigid fixation of the patient without certain elements distorting the terminal occlusion (bite block) or the soft tissue silhouette (chin rest). This embodiment can be particularly useful for larger image volumes, for example.

It is also of course to be understood that while the example embodiments of the present invention as described in FIGS. 1-6 relate generally to positioning of an orthodontic patient, it is of course to be understood that the present invention is not limited to such example application and that the present invention can be used in other applications or cone-beam tomography scans. Such applications may include, for example, medical applications such as craniofacial (diagnostics, treatment, prosthetics, etc.), other dental applications (diagnostics or treatment for hard tissue or soft tissue applications, etc.), and others. Such applications may also include, for example, non-medical applications such as in forensics.

Figure 7:
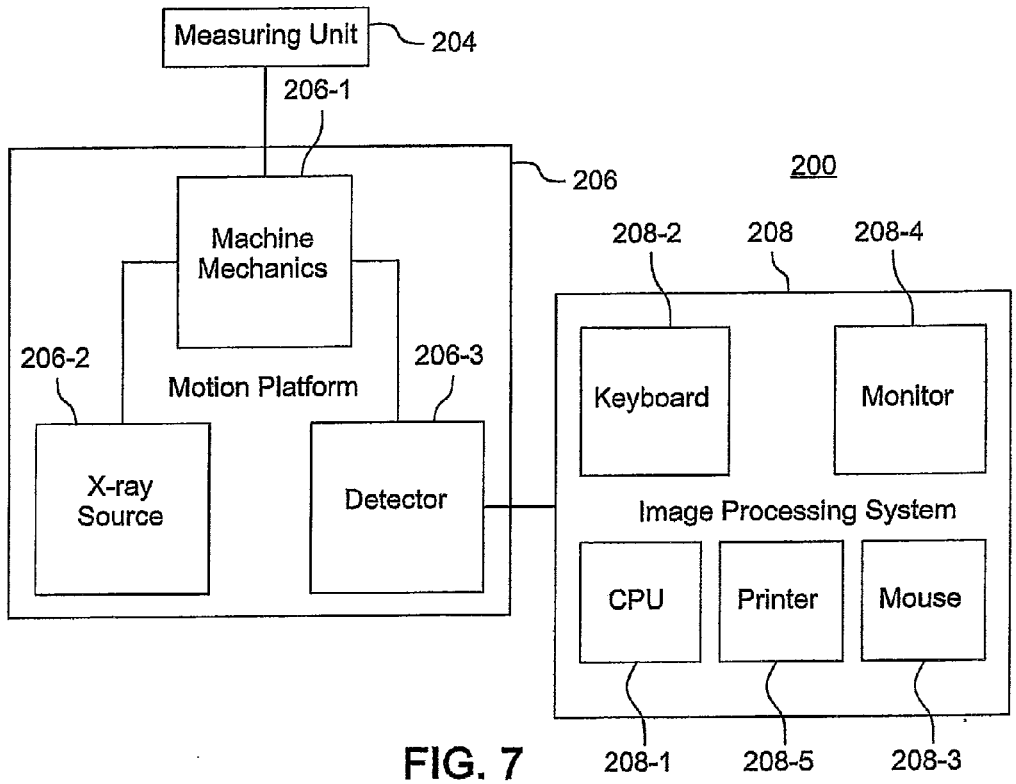
FIG. 7 is a block diagram showing in more detail a system 200 for cone-beam tomography according to an embodiment of the present invention.

FIG. 7 is a block diagram showing in more detail the system 200 for cone-beam tomography according to an embodiment of the present invention. The system 200 including the positioning device 10 shown in FIGS. 1-5 can enable optimal positioning of a patient such that the relevant anatomy, e.g., the condyles or soft tissue silhouette of the patient, can be registered within the image volume of the cone-beam tomography system 200.

The machine mechanics unit 206-1 of the motion platform 206 directs the x-ray source 206-2 and the x-ray detector 206-3 accordingly to perform scanning. The x-ray detector or receiver 206-3 may be large amorphous silicon thin film transistors (TFT), charge-coupled device (CCD) detectors coupled to image intensifiers, or any other suitable type of digital sensor or radiation receptor.

Scanning of the patient is performed and the digital data can be transmitted to an image processing system 208, from which it can be processed (e.g., to perform a three-dimensional reconstruction) and presented to the clinician and to the patient. The image processing system 208 can include a central processing unit (CPU) 208-1 and can process the signal to produce an image on an associated output device (such as the monitor 208-4 or the printer 208-5). The image processing system 208 allows the user to view and analyze the dental images that the system creates. The image processing system 208 may be, for example, a desktop, tower, laptop, or notebook computer, equipped with software for processing the data provided to it by the sensor 206-3. The image processing system 208 may be connected to or have built in one or more input devices, such as a keyboard 208-2 and a mouse 208-3, and one or more output devices, such as the display or monitor 208-4 and the printer 208-5.

These devices allow the user to view and analyze the dental images that the system creates through a graphical user interface, and can also allow the user to control the operation of the system. For example, an interface screen can enable a user to easily access the information and initiate analysis. The image processing system can also include or be connected to a storage device (not shown), such as a hard drive, for permanent storage of the images in patient files. Other potential storage devices include floppy disks, ZIP drives, magnetic tape, and optical medium. A variety of computer program products comprising, in general, a computer-readable medium, can be used with the present invention.

The software might run on a PC-compatible, Macintosh®, or Unix®-based computer, among others. In one embodiment the software runs on a PC-compatible computer with a Pentium®-based CPU running Windows 98®, Me®, 2000®, XP®, or Vista®. Of course, these examples are not meant to be limiting in any way, and the software can be written to be compatible with other or newer operating systems as well. In another embodiment, the software can be written to be complementary to that used for acquiring intra-oral images and for standard panoramic, video, and cephalometric examinations. The software also can preferably be compatible with dental practice management software.

The computer preferably contains at least 1 GB of RAM and, for example, 500 GB of hard disk space to store the software and image files. The display would preferably be optimized for video images in color. It might also be advantageous to bundle the system with a backup system for storing image and patient data.

The system 200 of FIG. 7 also includes one or more measuring units 204 such as a position sensor which can automatically take electrical measurements of the positions of various elements of device 10 (for example, the head clamp 18, the head rest 26, the forehead pad 33, etc.), after the patient is fitted therein or is positioned using the method of FIG. 6, for example. The measuring unit 204 can then transmit those measurements to a processor such as the image processing system 208 or to a separate processor (not shown).

The processor can calculate the position of the patient's relevant anatomy (e.g., the soft tissue silhouette or the condyles) with respect to the image volume from this data. For that purpose, the position of the ear tubes 16 with respect to the reference coordinate system of the cone-beam tomography system 200 can be calculated from the horizontal and vertical positions of the device 10 and the known geometric dimensions of the device 10 itself. Higher precision can be attained by including the width of the head clamp 18 in the calculation. With the well known and fixed spatial relation between the auditory canal and the condyles, the processor can calculate the position of the patient's condyles, for example, with respect to a reference coordinate system of the system 200. The system 200 thus knows a precise position of the patient and the position and shape of the image volume.

Using this information, the system 200 can calculate the set values for the horizontal and vertical position of the device 10 that would correspond to the image volume position. The system 200 can then optimize the positioning of the patient by directing the clinician to position or re-position the patient according to the calculated set values of the device 10. Such direction can take any suitable form, including audio instructions or visual instructions such as sounds (e.g, voice) or LEDs, for example, using known techniques. These instructions can be provided by the image processing system 208.

Alternatively, the processor can optimize positioning by (1) calculating the required image volume, given the position of the patient as calculated from the electrical measurements as described above, and (2) programming the motion platform 206 to achieve the required image volume. In this way, the position of the image volume can be optimized by the system 200 using known algorithms to ensure that the relevant anatomy (e.g., the condyles) lie completely inside the image volume, for example. The processor can adjust the scanning trajectory of the motion platform 206 based on the required image volume, e.g., by moving the rotational center of the motion platform with additional motors. Drive systems that allow such a movement are generally used in panoramic x-ray machines in various layouts. In any event, the processor can send programming signals to the machine mechanics unit 206-1 of the motion platform 206, which directs the x-ray source 206-2 and the x-ray detector 206-3.

Figure 8:
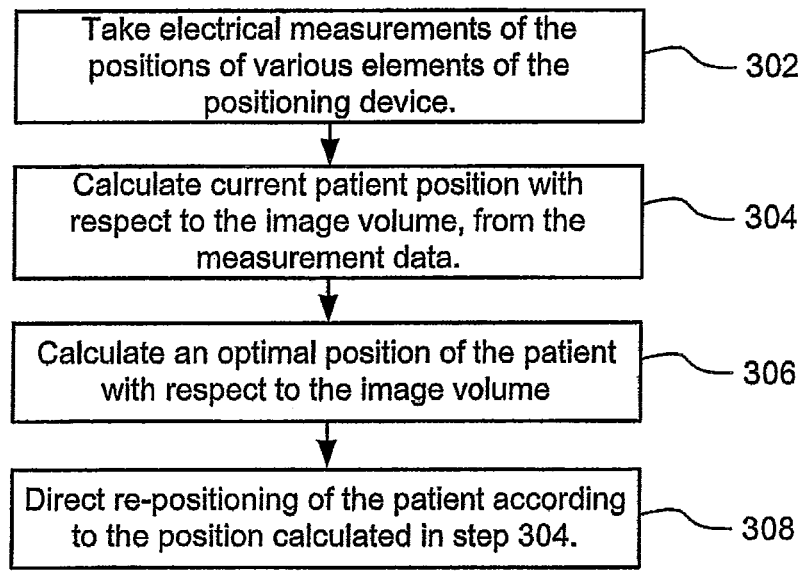
FIG. 8 is a flowchart showing a method for patient positioning in cone-beam tomography according to another embodiment of the present invention.

FIG. 8 is a flowchart showing a method 300 for patient positioning in cone-beam tomography according to another embodiment of the present invention. The method 300 can use a cone-beam tomography system such as system 200 of FIGS. 1-5, which includes positioning device 10. By virtue of the method shown in FIG. 8, the patient's relevant anatomy (e.g., the condyles or soft tissue silhouette) can be brought within the image volume 12 of the scan performed by the cone-beam tomography system 200, which can result in a more useful image. The method 300 of FIG. 8 can be implemented after the patient is fitted into device 10 or after the patient is positioned using the method of FIG. 6, for example. As an example, computer-readable medium can store a computer program which performs the steps of the method 300 of FIG. 8.

In step 302, the measuring unit 204 automatically (or in response to a user-instructed command or other type of command) takes electrical measurements of the positions of various elements of device 10 (for example, the head clamp 18, the head rest 26, the forehead pad 33, etc.). In step 304, those measurements are transmitted to a processor, such as the image processing system 208 or a separate processor (not shown), and the processor calculates the position of the patient's relevant anatomy (e.g., the condyles or soft tissue silhouette) with respect to the image volume from this measurement data.

For that purpose, the position of the ear tubes 16 with respect to the reference coordinate system of the cone-beam tomography system 200 can be calculated from the horizontal and vertical positions of the device 10 and the known geometric dimensions of the device 10 itself. Higher precision can be attained by including the width of the head clamp 18 in the calculation. With the well known and fixed spatial relation between the auditory canal and the condyles, the processor can calculate the position of the patient's condyles, for example, with respect to a reference coordinate system of the system 200. The system 200 thus knows a precise position of the patient and the position and shape of the image volume.

Using this information and known algorithms, in step 306 the system 200 calculates the set values for the horizontal and vertical position of the device 10 (and thus a positioning of the patient) that would optimally correspond to the image volume. In step 308, the system 200 then directs the clinician to position or re-position the patient according to the calculated set values of the device 10. Such direction can take any suitable form, including audio instructions or visual instructions such as sounds (e.g, voice) or LEDs, for example, using known techniques. These instructions can be provided by the image processing system 208.

Figure 9:
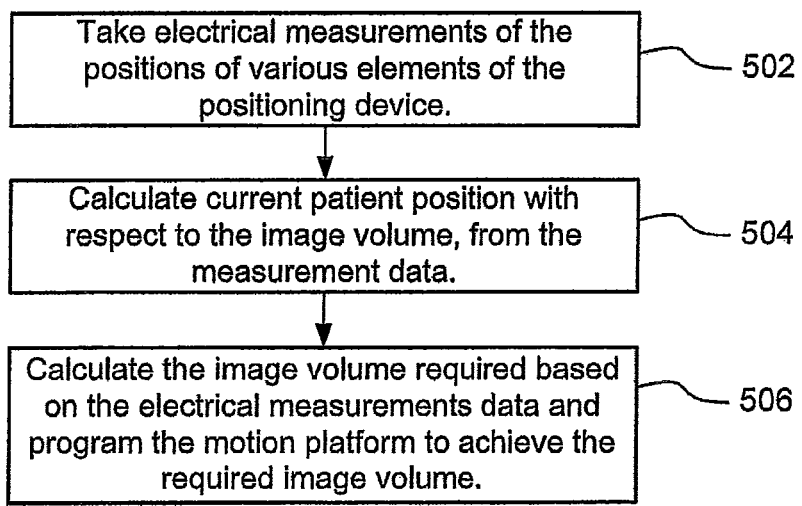
FIG. 9 is a flowchart showing a method for patient positioning in cone-beam tomography according to another embodiment of the present invention.

FIG. 9 is a flowchart showing a method 500 for patient positioning in cone-beam tomography according to another embodiment of the present invention. A computer-readable medium can store a computer program which performs the steps of the method 500 of FIG. 9.

Steps 502 and 504 of FIG. 9 are similar to steps 302 and 304 in FIG. 8. In step 506 of FIG. 9, the processor can optimize positioning by (1) calculating the required image volume, given the position of the patient as calculated from the electrical measurements as described above, and (2) programming the motion platform 206 to achieve the required image volume. In this way, the position of the image volume can be optimized by the system 200 using known algorithms to ensure that the relevant anatomy (e.g., the condyles) lie completely inside the image volume, for example. The processor can adjust the scanning trajectory of the motion platform 206 based on the required image volume, e.g., by moving the rotational center of the motion platform with additional motors. Drive systems that allow such a movement are generally used in panoramic x-ray machines in various layouts. In any event, the processor can send programming signals to the machine mechanics unit 206-1 of the motion platform 206, which directs the x-ray source 206-2 and the x-ray detector 206-3.

Figure 10:
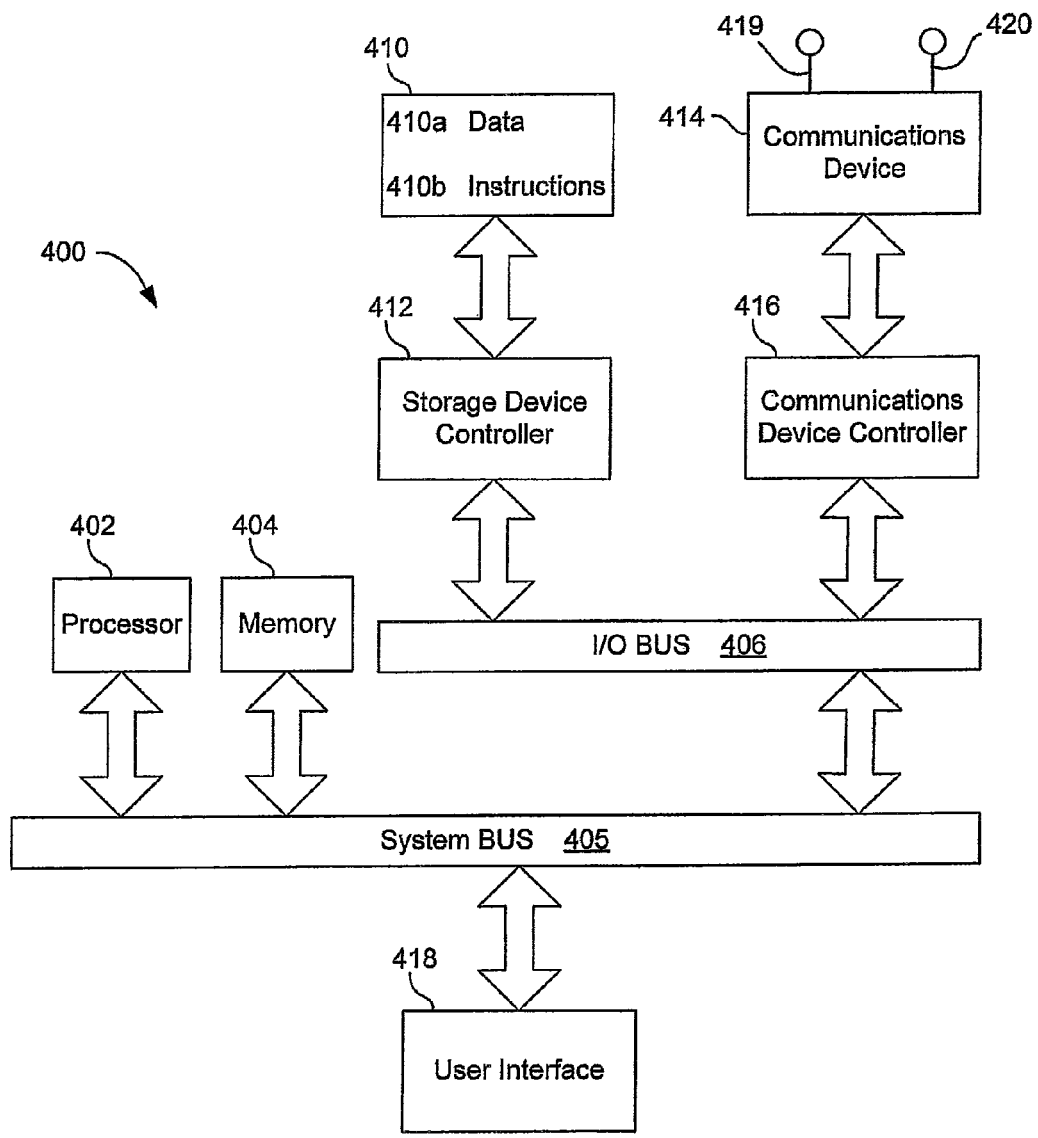
FIG. 10 is an architecture diagram of an example data processing system or device which can be used in connection with an embodiment of the present invention.

FIG. 10 is an architecture diagram of an example data processing system or device 400, which, according to an example embodiment, can form individual ones of the components 204, 206-1, and 208 of FIG. 7. Data processing system 400 includes a processor 402 coupled to a memory 404 via system bus 406. Processor 402 is also coupled to external Input/Output (I/O) devices (not shown) via the system bus 406 and an I/O bus 408, and at least one input/output user interface 418. Processor 402 may be further coupled to a communications device (interface) 414 via a communications device controller 416 coupled to the I/O bus 408. Processor 402 uses the communications device 414 to communicate with a network, such as, for example, a network as shown in FIG. 7, and the device 414 may have one or more input and output ports. Device 414 has a data port 419 operably coupled to a network for sending and receiving data, and may also have one or more additional input and output ports. A storage device 410 having a computer-readable medium is coupled to the processor 402 via a storage device controller 412 and the I/O bus 408 and the system bus 406. Processor 402 also can include an internal clock (not shown) to keep track of time, periodic time intervals, and the like.

The input/output user interface 418 may include, for example, at least one of a keyboard, a mouse, a trackball, touch screen, a keypad, and/or any other suitable type of user-operable input device(s), and at least one of a video display, a liquid crystal or other flat panel display, a speaker, a printer, and/or any other suitable type of output device for enabling a user to perceive outputted information.

Processing can be performed, for example, by a processor that communicates with the measuring unit 204 and the cone-beam tomography machine, by a processor embedded in the machine, or by any other suitable arrangement. The processor can read the data from, e.g., the measuring unit 204 and generate a scanning trajectory or instructions for the clinician for the cone-beam tomography machine. Modulation of mA of the x-ray source may also be implemented.

Storage device 410 having a computer readable medium is coupled to the processor 402 via a storage device controller 412 and the I/O bus 408 and the system bus 406. The storage device 410 is used by the processor 402 and controller 412 to store and read/write data 410a, and to store program instructions 410b used to implement at least part of the procedures described and shown herein. The storage device 410 also stores various routines and operating programs (e.g., Microsoft Windows, UNIX®/LINUX®, or OS/2®) that are used by the processor 402 for controlling the overall operation of the system 400. At least one of the programs (e.g., Microsoft Winsock®) stored in storage device 410 can adhere to TCP/IP protocols (i.e., includes a TCP/IP stack), for implementing a known method for connecting to the Internet or another network, and may also include web browser software, such as, for example, Microsoft Internet Explorer (IE) and/or Netscape Navigator, for enabling a user of the system 400 to navigate or otherwise exchange information with the World Wide Web (WWW).

In operation, processor 402 loads the program instructions 410b from the storage device 410 into the memory 404. Processor 402 then executes the loaded program instructions 410b to perform any of the example methods described herein, for operating the system 200.

The present invention or any part(s) or function(s) thereof may be implemented using hardware, software or a combination thereof and may be implemented in one or more computer systems or other processing systems. It is noted that the various components of the present invention may be controlled by one or more modules coupled to the various components. The modules can operate in accordance with software control programs and operating routines stored in an associated memory or memories. The modules and their sub-modules can write and/or read information to/from the memory or memories, and in this way, can perform operations in accordance with the system, method, and apparatus of the present invention. The modules may be implemented using hardcoded computational modules or other types of circuitry, or a combination of software and circuitry modules. Software routines for performing the modules can, in one embodiment, be stored as instructions in a memory and can be executed by a processor of a control module.

In an embodiment where the invention or any part(s) or function(s) thereof are implemented using software, the software may be stored in a computer program product, a computer program medium, or a computer-readable medium, and loaded into a computer system using a removable storage drive, a hard drive, or a communications interface. The control logic (software), when executed by a processor, causes the processor to perform the functions of the invention as described herein.

In this document, the terms "computer program medium" and "computer usable medium" are used to refer generally to media such as a removable storage drive, a hard disk installed in a hard disk drive, and signals. Also, "computer-readable medium" is used to refer generally to media such as a storage drive, CD, hard drive or other tangible object that can store a program. These computer program products provide software to the system.

While various embodiments of the present invention have been described above, it should be understood that they have been presented by way of example, and not limitation. It will be apparent to persons skilled in the relevant art(s) that various changes in form and detail can be made therein without departing from the spirit and scope of the present invention. Thus, the present invention should not be limited by any of the above described exemplary embodiments, but should be defined only in accordance with the following claims and their equivalents.

What is claimed is:

1. A device for positioning a patient, the device comprising:
   a volume indicator that includes:
      a boundary structure that delineates a portion of an outer boundary of an image volume, the image volume being a volume of space through which x-rays, emitted by an x-ray source, pass through at each of a plurality of scanning positions during a scanning operation, wherein a contour of the boundary structure matches a contour of the portion of the outer boundary of the image volume, and
      a structure for horizontal alignment that delineates another portion of the outer boundary of the image volume, wherein a contour of the structure for horizontal alignment matches a contour of the other portion of the outer boundary of the image volume; and
   a head clamp adapted to position at least a portion of a head of the patient within the outer boundary of the image volume,
   wherein the device is attached to a tomography system that includes the x-ray source.

2. The device as defined in claim 1, wherein the head clamp comprises:
   a plurality of ear tubes disposed at ends of the head clamp for restricting lateral movement of the head of the patient and for facilitating alignment of the head of the patient in a substantially horizontal plane relative to the structure for horizontal alignment, and
a forehead alignment mechanism that includes a forehead pad for restricting forward movement of the head of the patient,
wherein the plurality of ear tubes are positionable such that an axis through the plurality of ear tubes can be parallel to a plane defined by the structure for horizontal alignment.

3. The device as defined in claim 1, wherein the portions of the outer boundary of the image volume respectively delineated by the boundary structure and the structure for horizontal alignment correspond to a front boundary of the image volume.

4. The device as defined in claim 1, wherein the boundary structure is a parabolically shaped vertical structure, and
wherein the outer boundary of the image volume defines an outer boundary for the patient to be positioned within in order for a patient's condyles to appear within a tomographic image.

5. The device as defined in claim 1, wherein a front part of the outer boundary is spherical.

6. The device as defined in claim 1, wherein a front part of the outer boundary is cylindrical.

7. The device as defined in claim 1, wherein the structure for horizontal alignment is a horizontal structure.

8. The device as defined in claim 1, wherein the head clamp is adjustable.

9. The device as defined in claim 1, further comprising:
a measuring unit adapted to measure a position of the head clamp;
a calculating unit adapted to calculate a position of the patient based on a result obtained by the measuring unit; and
a directing unit adapted to direct re-positioning of the patient based on a result obtained by the calculating unit.

10. The device as defined in claim 1, further comprising:
a measuring unit adapted to measure a position of the head clamp;
a calculating unit adapted to calculate a position of the patient based on a result obtained by the measuring unit; and
a programming unit adapted to program a scanning trajectory of the tomography system based on a result obtained by the calculating unit.

11. The device as defined in claim 1, further comprising:
a measuring unit adapted to measure a position of the head clamp;
a calculating unit adapted to calculate a position of the patient based on a result obtained by the measuring unit; and
a programming unit adapted to adjust x-ray parameters of the tomography system based on a result obtained by the calculating unit.

12. A device for positioning a patient, the device comprising:
a head clamp that includes a plurality of ear tubes attached at respective ends and adapted to contact the patient in the patient's auditory canals such that condyles of the patient are registered with respect to an image volume, the image volume being a volume of space through which x-rays, emitted by an x-ray source, pass through at each of a plurality of scanning positions during a scanning operation, and a head support adapted to restrict movement of the patient; and
a volume indicator that includes:
a boundary structure that delineates a portion of an outer boundary of the image volume, wherein a contour of the boundary structure matches a contour of the portion of the outer boundary of the image volume, and
a structure for horizontal alignment which delineates another portion of the outer boundary of the image volume, wherein a contour of the structure for horizontal alignment matches a contour of the other portion of the outer boundary of the image volume, and
wherein the device is attached to a tomography system that includes the x-ray source.

13. The device as defined in claim 12, wherein the head support restricts movement of the patient in a front direction.

14. The device as defined in claim 12 or 13, wherein the head support restricts movement of the patient in a rear direction.

15. A method of positioning a patient for a scanning operation by a tomography system, comprising the steps of:
restricting lateral movement of a head of the patient;
aligning the head of the patient in a substantially horizontal plane relative to a structure for horizontal alignment;
restricting forward movement of the head of the patient; and
using a volume indicator to check that at least a portion of the head of the patient is within an outer boundary of an image volume, the image volume being a volume of space through which x-rays, emitted by an x-ray source, pass through at each of a plurality of scanning positions during a scanning operation,
wherein the volume indicator includes a boundary structure that delineates a portion of the outer boundary of the image volume,
wherein a contour of the boundary structure matches a contour of the portion of the outer boundary of the image volume,
wherein the volume indicator includes the structure for horizontal alignment which delineates another portion of the outer boundary of the image volume, and
wherein a contour of the structure for horizontal alignment matches a contour of the other portion of the outer boundary of the image volume.

16. The method as defined in claim 15, wherein the portions of the outer boundary of the image volume respectively delineated by the boundary structure and the structure for horizontal alignment correspond to a front boundary of the image volume.

17. The method as defined in claim 15, wherein the volume indicator at least partially encloses physical space that is coincident with at least a portion of the image volume of the tomography system.

18. The method as defined in claim 15, wherein a front part of the outer boundary of the image volume is spherical.

19. The method as defined in claim 15, wherein a front part of the outer boundary of the image volume is cylindrical.

20. A method of performing a scanning operation with a tomography system, comprising the steps of:
restricting lateral movement of a head of a patient;
aligning the head of the patient in a substantially horizontal plane relative to a structure for horizontal alignment;
restricting forward movement of the head of the patient;
using a volume indicator to check that at least a portion of the head of the patient is within an outer boundary of an image volume, the image volume being a volume of space through which x-rays, emitted by an x-ray source, pass through at each of a plurality of scanning positions during the scanning operation, wherein the volume indicator includes a boundary structure that delineates a portion of the outer boundary of the volume indicator, wherein a contour of the boundary structure matches a contour of the portion of the outer boundary of the image volume, wherein the volume indicator includes the structure for horizontal alignment that delineates another portion of the outer boundary of the image volume, and wherein a contour of the structure for horizontal alignment matches a contour of the other portion of the outer boundary of the image volume;

rotating the x-ray source and a detector around the head of the patient to create a plurality of two-dimensional images respectively corresponding to the plurality of scanning positions; and creating a three-dimensional image based on the plurality of two-dimensional images.

21. The method as defined in claim 20, wherein a front part of the outer boundary is spherical.

22. The method as defined in claim 20, wherein a front part of the outer boundary is cylindrical.

\* \* \* \* \*